US00PP34787P2

(12) United States Plant Patent
van Sambeek

(10) Patent No.: US PP34,787 P2
(45) Date of Patent: Nov. 29, 2022

(54) ***GAURA* PLANT NAMED 'DOGAURGRAPI'**

(50) Latin Name: *Gaura lindheimeri*
Varietal Denomination: DOGAURGRAPI

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/831,431

(22) Filed: Jun. 2, 2022

(51) Int. Cl.
*A01H 5/02* (2018.01)
*A01H 6/00* (2018.01)

(52) U.S. Cl.
USPC ..... Plt./432

(58) Field of Classification Search
USPC ..... Plt./432
See application file for complete search history.

*Primary Examiner* — Annette H Para
(74) *Attorney, Agent, or Firm* — C. Anne Whealy

(57) ABSTRACT

A new and distinct cultivar of *Gaura* plant named 'DOGAURGRAPI', characterized by its compact and upright to outwardly spreading plant habit; vigorous growth habit and rapid growth rate; freely branching habit; freely flowering habit; bright pink-colored flowers; and good garden performance.

1 Drawing Sheet

Botanical designation: *Gaura lindheimeri.*
Cultivar denomination: 'DOGAURGRAPI'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Feb. 4, 2022, application number 2022/0381. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Gaura* plant, botanically known as *Gaura lindheimeri* and hereinafter referred to by the name 'DOGAURGRAPI'.

The new *Gaura* is a product of a planned breeding program conducted by the Inventor in Aalsmeer, The Netherlands. The objective of the breeding program is to create new compact and early-flowering *Gaura* plants with attractive leaf and flower coloration.

The new *Gaura* plant originated from a cross-pollination in June, 2016 in Aalsmeer, The Netherlands of a proprietary selection of *Gaura lindheimeri* identified as code number GR-0007, not patented, as the female, or seed, parent with a proprietary selection of *Gaura lindheimeri* identified as code number GR14-000046-008, not patented, as the male, or pollen, parent. The new *Gaura* plant was discovered and selected by the Inventor as a single flowering plant from within the progeny of the stated cross-pollination in a controlled environment in Aalsmeer, The Netherlands in June, 2017.

Asexual reproduction of the new *Gaura* plant by vegetative tip cuttings in a controlled environment in Aalsmeer, The Netherlands since July, 2017 has shown that the unique features of this new *Gaura* plant are stable and reproduced true to type in successive generations.

SUMMARY OF THE INVENTION

Plants of the new *Gaura* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DOGAURGRAPI'. These characteristics in combination distinguish 'DOGAURGRAPI' as a new and distinct *Gaura* plant:

1. Compact and upright to outwardly spreading plant habit.
2. Vigorous growth habit and rapid growth rate.
3. Freely branching habit.
4. Freely flowering habit.
5. Bright pink-colored flowers.
6. Good garden performance.

Plants of the new *Gaura* can be compared to plants of the female parent selection. Plants of the new *Gaura* differ from plants of the female parent selection in flower color as plants of the new *Gaura* have bright pink-colored flowers whereas plants of the female parent selection have white-colored flowers.

Plants of the new *Gaura* can be compared to plants of the male parent selection. Plants of the new *Gaura* differ from plants of the male parent selection in flower color as plants of the new *Gaura* have bright pink-colored flowers whereas plants of the male parent selection have white-colored flowers.

Plants of the new *Gaura* can be compared to plants of *Gaura lindheimeri* 'Belezza White', not patented. In side-by-side comparisons, plants of the new *Gaura* differ from plants of 'Belezza White' in the following characteristics:

1. Plants of the new *Gaura* are more compact than and not as tall as plants of 'Belezza White'.
2. Plants of the new *Gaura* have bright pink-colored flowers whereas plants of 'Belezza White' have white-colored flowers.

Plants of the new *Gaura* can also be compared to plants of *Gaura lindheimeri* 'Gaudi Red', not patented. In side-by-side comparisons, plants of the new *Gaura* differ from plants of 'Gaudi Red' in the following characteristics:

1. Plants of the new *Gaura* have green-colored leaves whereas plants of 'Gaudi Red' have reddish-colored leaves.
2. Plants of the new *Gaura* have bright pinke-colored flowers whereas plants of 'Gaudi Red' have dark reddish pink- colored flowers.

BRIEF DESCRIPTION OF THE PHOTOGRAPH

The accompanying colored photograph illustrates the overall appearance of the new *Gaura* plant showing the colors as true as it is reasonably possible to obtain in colored reproductions of this type. Colors in the photograph may differ slightly from the color values cited in the detailed botanical description which accurately describe the colors of the new *Gaura* plant.

The photograph is a side perspective view of a typical plant of 'DOGAURGRAPI' grown in a container.

DETAILED BOTANICAL DESCRIPTION

The aforementioned photographs and following observations, measurements and values describe plants grown during the early summer in 17-cm containers in an outdoor nursery in Aalsmeer, The Netherlands and under cultural practices typical of commercial *Gaura* production. During the production of the plants, day temperatures averaged 21° C. and night temperatures averaged 15° C. Plants were pinched one time one week after planting and were 16 weeks old when the photograph and description were taken. In the following description, color references are made to The Royal Horticultural Society Colour Chart, Second Edition, except where general terms of ordinary dictionary significance are used.

Botanical classification: *Gaura lindheimeri* 'DOGAURGRAPI'.

Parentage:

*Female, or seed, parent*.—Proprietary selection of *Gaura lindheimeri* identified as code number GR-0007, not patented.

*Male or pollen parent*.—Proprietary selection of *Gaura lindheimeri* identified as code number GR14-000046-008, not patented.

Propagation:

*Type*.—By vegetative tip cuttings.

*Time to initiate roots, summer*.—About ten days at temperatures about 26° C.

*Time to initiate roots, winter*.—About two weeks at temperatures about 23° C.

*Time to produce a rooted young plant, summer*.—About twelve days at temperatures about 23° C.

*Time to produce a rooted young plant, winter*.—About 16 days at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous perennial; compact and upright to outwardly spreading plant habit; freely basal branching habit with about nine primary branches each with about 24 secondary branches developing per plant, pinching enhances lateral branch development; dense and bushy plant form; vigorous growth habit and rapid growth rate.

*Plant height*.—About 30 cm.

*Plant diameter*.—About 50 cm.

Lateral branch description:

*Length*.—About 25 cm.

*Diameter*.—About 2 mm.

*Internode length*.—About 2 cm.

*Strength*.—Strong.

*Aspect*.—Upright to about 60° from vertical.

*Texture and luster*.—Pubescent, rough; glossy.

*Color, developing and developing*.—Close to 143A tinged with close to 53A.

Leaf description:

*Arrangement*.—Alternate, simple; sessile.

*Length*.—About 9 cm.

*Width*.—About 1.4 cm.

*Shape*.—Linear.

*Apex*.—Acute.

*Base*.—Attenuate.

*Margin*.—Entire with shallow and widely-spaced indentations.

*Texture and luster, upper and lower surfaces*.—Smooth, glabrous; glossy.

*Venation pattern*.—Pinnate.

*Color*.—Developing and fully expanded leaves, upper surface: Close to 147A; venation, close to 59A. Developing and fully developed leaves, lower surface: Close to 147B; venation, close to 147B.

Flower description:

*Flower arrangement and habit*.—Single flowers arranged on terminal and axillary racemes; freely flowering habit with about 14 flowers per inflorescence and about 1,378 flowers developing per plant during the flowering season; flowers face mostly upright to outwardly.

*Fragrance*.—None detected.

*Natural flowering season*.—Plants flower continuously from July to September in The Netherlands; plants begin flowering about eleven weeks after planting; flowers not persistent.

*Inflorescence height*.—About 15 cm.

*Inflorescence diameter*.—About 6 cm.

*Flower diameter*.—About 1.3 cm by 2.6 cm.

*Flower depth (height)*.—About 2.6 cm.

*Flower buds*.—Length: About 1.8 cm. Diameter: About 4 mm. Shape: Elongated oblong. Texture and luster: Smooth, glabrous; matte. Color: Close to 73A.

*Petals*.—Arrangement: Four in a single whorl. Length: About 1.6 cm. Width: About 1.1 cm. Shape: Spatulate. Apex: Obtuse. Base: Attenuate. Margin: Entire. Texture and luster, upper and lower surfaces: Smooth, glabrous; matte. Color: When opening, upper and lower surfaces: Close to 73A. Fully opened, upper and lower surfaces: Close to 73A; venation, close to 74A; color becoming closer to 68A with subsequent development.

*Sepals*.—Arrangement: Four in a single whorl. Length: About 1.5 cm. Width: About 2 mm. Shape: Linear. Apex: Acuminate. Base: Fused. Margin: Entire. Texture and luster, upper and lower surfaces: Smooth, glabrous; glossy. Color, upper and lower surfaces: Close to 185A.

*Pedicels*.—Length: About 14 cm. Diameter: About 1 mm. Strength: Moderately strong. Aspect: About 10° from stem axis. Texture and luster: Pubescent, rough; glossy. Color: Close to 187A.

*Reproductive organs*.—Stamens: Quantity: Eight per flower. Filament length: About 9 mm. Filament color: Close to 65B. Anther shape: Linear; basifixed. Anther size: About 1 mm by 4 mm. Anther color: Close to 187A. Pollen amount: Abundant. Pollen color: Close to 4C. Pistils: Quantity: One per flower. Pistil length: About 2 cm. Style length: About 1.3 cm. Style color: Close to 186A. Stigma shape: Four-lobed. Stigma diameter: About 3 mm. Stigma color: Close to 144C. Ovary color: Close to 187A. Fruits: To date, fruit development has not been observed on plants of the new *Gaura*.

Garden performance: Plants of the new *Gaura* have been observed to have good garden performance and tolerate wind, rain and temperatures ranging from about −23° C. to about 35° C. and to be suitable for U.S.D.A. Hardiness Zones 6 to 10.

Pathogen & pest resistance: To date, plants of the new *Gaura* have not been observed to be resistant to pathogens and pests common to *Gaura* plants.

It is claimed:

1. A new and distinct *Gaura* plant named 'DOGAUR-GRAPI' as illustrated and described.

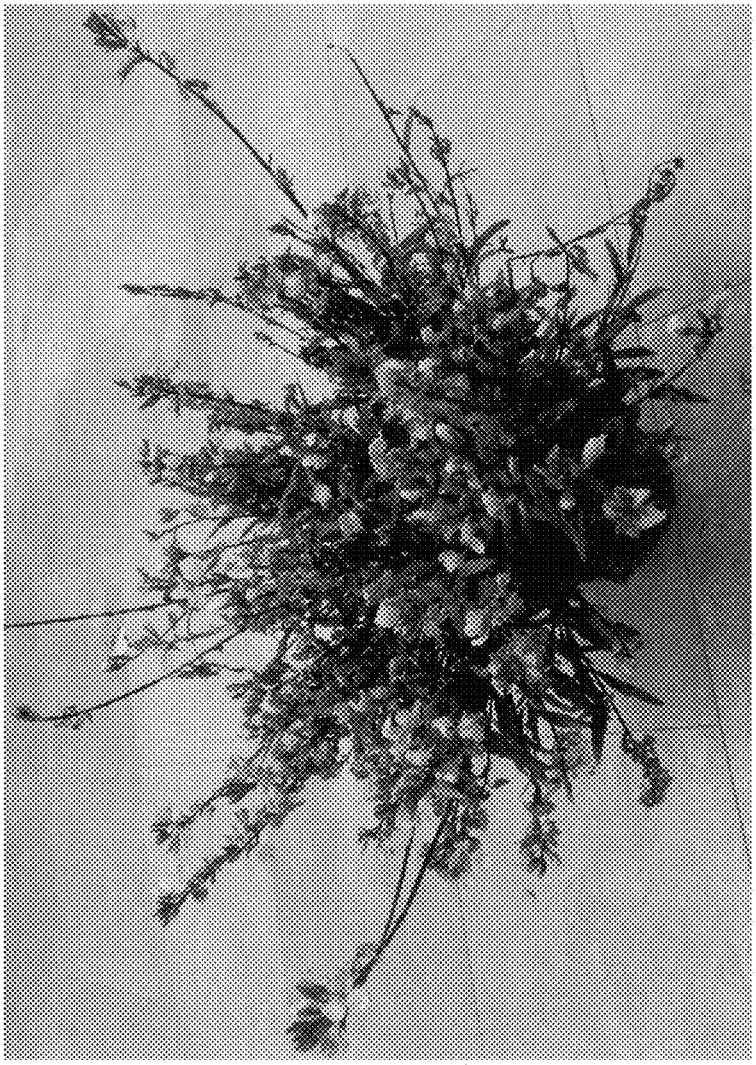

* * * * *